United States Patent
Gianesello et al.

(10) Patent No.: US 7,575,760 B2
(45) Date of Patent: Aug. 18, 2009

(54) CHEWABLE TABLET CONTAINING LYSINE

(75) Inventors: Valter Gianesello, Origlio (CH); Claudia Cappellini, Porza (CH); Michael David Marocchi, Delta (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/280,738

(22) Filed: Nov. 16, 2005

(65) Prior Publication Data

US 2006/0068023 A1 Mar. 30, 2006

Related U.S. Application Data

(63) Continuation of application No. 10/254,246, filed on Sep. 25, 2002, now Pat. No. 7,070,804.

(60) Provisional application No. 60/332,693, filed on Nov. 14, 2001.

(30) Foreign Application Priority Data

Oct. 23, 2001 (DE) .......................... 101 52 169

(51) Int. Cl.
*A61K 9/20* (2006.01)

(52) U.S. Cl. .................... 424/464; 424/465
(58) Field of Classification Search .......... 424/464, 424/465
See application file for complete search history.

(56) References Cited

U.S. PATENT DOCUMENTS

| 2,887,437 | A | * | 5/1959 | Oscar et al. |
| 3,970,750 | A | * | 7/1976 | Brockemeyer et al. |
| 4,638,013 | A | * | 1/1987 | Moja et al. |
| 5,432,160 | A | * | 7/1995 | Hara et al. |
| 6,352,713 | B1 | * | 3/2002 | Kirschner et al. |

FOREIGN PATENT DOCUMENTS

| EP | 1 219 182 A2 | 7/2002 |
| FR | 2 215 950 A | 8/1974 |

* cited by examiner

*Primary Examiner*—Humera N Sheikh
(74) *Attorney, Agent, or Firm*—Michael P. Morris; Mary Ellen M. Devlin; Timothy X. Witkowski

(57) ABSTRACT

A tablet with enhanced compliance by humans, in particular children and/or juveniles, comprising:
(a) a vitamin;
(b) lysine or a pharmaceutically acceptable salt thereof;
(c) a sweetener; and
(d) a pharmaceutically or dietetically acceptable carrier.

9 Claims, No Drawings

CHEWABLE TABLET CONTAINING LYSINE

RELATED APPLICATIONS

This application is a continuation of U.S. application Ser. No. 10/254,246, filed Sep. 25, 2002, now U.S. Pat. No. 7,070,804, which claimed benefit under 35 U.S.C. §119(e) of prior U.S. Provisional application Ser. No. 60/332,693, filed Nov. 14, 2001.

FIELD OF THE INVENTION

The present invention relates to a tablet with enhanced compliance by humans, in particular children and/or juveniles comprising at least one vitamin, optionally at least one mineral, and lysine or a pharmaceutically acceptable salt thereof.

BACKGROUND OF THE INVENTION

It is known that lysine as an essential amino acid enhances appetite and, together with vitamin $D_3$, improves the absorption of calcium. The prior art dealing with lysine as nutritional supplement may be best illustrated by the following references: A. A. Albanese et al., NY State J. Med. 1955; 55, 3453-3456 describe lysine supplementation in infant feeding. G. G. Graham et al., Am. J. Clin. Nutr. 1969; 22 (11), 1459-1468 describe the effect of lysine enrichment of wheat flour for the evaluation in infants. R. Civitelli et al., Nutrition 1992; 8 (6), 400-405, disclose the metabolism of (L)-lysine and calcium in humans. P. Fürst, Nutrition 1993; 9 (1), 71-72 suggests (L)-lysine as a nutritional tool in the prophylaxis and treatment of osteoporosis. N. W. Flodin, J. Am. Coll. Nutr. 1997; 16 (1), 7-21, reviews the metabolic roles, the pharmacology and the toxicology of lysine.

Accordingly, there is a need to provide humans, in particular children and/or juveniles, with lysine supplementation. However, children will hardly accept chewable tablets which contain effective amounts of lysine due to its disgusting taste. The problem underlying the present invention was to provide a lysine containing chewable tablet which is well accepted by children and/or juveniles.

SUMMARY OF THE INVENTION

The invention relates to a tablet with enhanced compliance by humans comprising the following constituents:
  (a) at least one vitamin,
  (b) optionally at least one mineral,
  (c) lysine or a pharmaceutically acceptable salt thereof,
  (d) at least one sweetener and optionally at least one flavoring agent having the capability of masking the disgusting flavor of lysine,
  (e) and a pharmaceutically or dietetically acceptable carrier.

Another aspect of the present invention is a method of improving the physiological state of humans which method comprises administering an effective amount of the tablet according to the present invention.

Furthermore, the invention relates to a method for the manufacture of a tablet according to the present invention which method comprises mixing of the different components (a) to (e) and tabletting by direct compression.

DETAILED DESCRIPTION OF THE INVENTION

The invention relates in particular to tablets to be sucked or chewed by children and/or juveniles wherein the disgusting taste caused by lysine is masked.

Specifically the subject matter of this invention provides tablets intended for the oral way, to be sucked or to be chewed, containing as active ingredients lysine, one or more vitamins, and optionally one or more minerals. Lysine is preferably provided in form of a pharmaceutically acceptable salt, in particular as (L)-lysine monohydrochloride. Most preferably the tablet comprises 10 mg to 100 mg, in particular about 50 mg of (L)-lysine monohydrochloride per unit dosage.

Preferably component (a) comprises at least one vitamin selected from the group consisting of retinol equivalents such as β-carotene or vitamin A, vitamin B such as vitamin $B_1$, vitamin $B_2$, vitamin $B_6$, or vitamin $B_{12}$, vitamin C, vitamin D such as vitamin $D_3$, vitamin E, folic acid, vitamin H, and vitamin PP.

The ranges of amounts of ingredients given hereinabove and hereinbelow relate to the declared amount of said ingredients and include appropriate stability overdosages.

Most preferably component (a) is a mixture of vitamins consisting essentially of 0.4 mg to 0.8 mg, in particular about 0.5 mg to 0.7 mg of β-carotene, 500 IU to 1500 IU, in particular about 700-1100 IU of vitamin A palmitate, 0.3 mg to 1.0 mg, in particular about 0.4 mg to 0.6 mg of vitamin $B_1$ nitrate, 0.3 mg to 1.0 mg, in particular about 0.5 mg to 0.7 mg of vitamin $B_2$, 0.3 mg to 1.0 mg, in particular about 0.5 mg to 0.7 mg of vitamin $B_6$ hydrochloride, 0.4 μg to 1.0 μg, in particular about 0.5 μg to 0.9 μg of vitamin $B_{12}$, 15 mg to 40 mg, in particular about 20 mg to 30 mg of vitamin C, 100 IU to 300 IU, in particular about 125 IU to 200 IU of vitamin $D_3$, 3.0 mg to 9.5 mg, in particular about 4.0 mg to 6.5 mg of vitamin E acetate, 20 μg to 80 μg, in particular about 40 μg to 70 μg of folic acid, 10 μg to 25 μg, in particular about 14 μg to 21 μg of vitamin H, and 4 mg to 10 mg, in particular about 5 mg to 8 mg of vitamin PP per unit dosage.

Preferably component (b) comprises at least one mineral selected from the group consisting of manganese such as manganese (II) gluconate, copper such as copper (II) carbonate, calcium such as dicalcium phosphate anhydrous, iron such as ferrous (II) fumarate, zinc such as zinc oxide and magnesium such as magnesium oxide.

Most preferably component (b) is a mixture consisting essentially of 0.2 mg to 0.8 mg, in particular about 0.4 mg to 0.6 mg of copper (II) carbonate, 150 mg to 300 mg, in particular about 200 mg to 250 mg of dicalcium phosphate anhydrous, 8 mg to 20 mg, in particular about 11 mg to 14 mg of ferrous (II) fumarate, 4 mg to 9 mg, in particular about 6 mg to 7 mg of zinc oxide and 12 mg to 28 mg, in particular about 18 mg to 21 mg of magnesium oxide per unit dosage.

Preferably component (d) contains at least one sweetener selected from the group consisting of calcium saccharinate, ammonium cyclamate, ammonium glycirhizinate, aspartame (N-L-α-aspartyl-L-phenylalanine 1-methylester), glucose and glucitols such as inositol, mannitol, sorbitol or dulcitol and at least one flavoring agent selected from the group consisting of natural citrus or orange flavor and PROSWEET® (manufactured by Virginia Dare Co., Inc.), which is a commercially available natural flavoring.

Most preferably component (d) consists essentially of 1.0 mg to 10.0 mg, in particular 4.0 mg to 8.0 mg of aspartame, 100.0 mg to 400.0 mg, in particular 200.0 mg to 350.0 mg of glucose, 200 mg to 800 mg, in particular 300 mg to 700 mg of sorbitol, 5.0 mg to 50.0 mg, in particular 10.0 mg to 30.0 mg of natural orange flavor and 1.0 mg to 10.0 mg, in particular 2.0 mg to 6.0 mg of PROSWEET® per unit dosage.

Preferably component (e) comprises at least one carrier selected from the group consisting of diluents, excipients, sticking agents, bulk agents, preservatives, colorants and other pharmaceutical or food processing agents.

Among the suitable excipients or diluents, it may particularly be cited acidifying or buffering agents such as citric acid, urea, or glycine, bulk agents such or mannitol or sorbitol, adhering agents with low speed of dissolution such as alkyl cellulose, for example, methyl cellulose, ethylcellulose, hydroxypropyl cellulose, hydroxypropyl methyl cellulose or carboxy methyl cellulose or copolymers of methacrylic and acrylic acid; binding agents such as silicon dioxide, polyvinyl pyrrolidone, arabic gum, guar gum, adraganth gum, or karaya gum, lubricating agents such as magnesium stearate, inert diluents such as lactose, gelatin, starch, mono- or diglyceride fatty acids, edible fat, sodium aluminium silicate, hydrogenated vegetable oil, calcium carbonate, magnesium phosphate, or calcium sulfate; skim milk powder, and sodium caseinate.

Among the suitable colorants, it may particularly be cited Turmeric powder (E100), Carmine powder (E120), β-carotene and Sunset Yellow (E110), Beetroot Red (E162), Erythrosine Red (E127), or a combination of these colorants.

Most preferred is a tablet which can be chewed or sucked with enhanced compliance by children and/or juveniles, preferably at an age of 4 to 16, in particular 6 to 14 years comprising the following constituents:

(a) a mixture of vitamins consisting essentially of 0.4 mg to 0.8 mg of β-carotene, 500 IU to 1500 IU of vitamin A palmitate, 0.3 mg to 1.0 mg of vitamin $B_1$ nitrate, 0.3 mg to 1.0 mg of vitamin $B_2$, 0.3 mg to 1.0 mg of vitamin $B_6$ hydrochloride, 0.4 μg to 1.0 μg of vitamin $B_{12}$, 15 mg to 40 mg of vitamin C, 100 IU to 300 IU of vitamin $D_3$, 3.0 mg to 9.5 mg of vitamin E acetate, 20 μg to 80 μg of folic acid, 10 μg to 25 μg of vitamin H, and 4 mg to 10 mg of vitamin PP per unit dosage, (b) a mixture of minerals consisting essentially of 0.2 mg to 0.8 mg of copper (II) carbonate, 150 mg to 300 mg of dicalcium phosphate anhydrous, 8.0 mg to 20 mg of ferrous (II) fumarate, 4 mg to 9 mg of zinc oxide and 12 mg to 28 mg of magnesium oxide per unit dosage, (c) 10 mg to 100 mg of (L)-lysine monohydrochloride per unit dosage, (d) a mixture of sweeteners and flavoring agents consisting essentially of 1.0 mg to 10.0 mg of aspartame, 5.0 mg to 50.0 mg of glucose syrup, 200 mg to 800 mg of sorbitol, 5.0 mg to 50.0 mg of natural orange flavor and 1.0 mg to 10.0 mg of PROSWEET® per unit dosage;

(e) a pharmaceutically or dietetically acceptable carrier, wherein the complete dosage unit weighs 500 mg to 2000 mg.

Another aspect of the present invention resides in a method of improving the physiological state of humans, in particular improving the development and growth of children and/or juveniles, most preferably at an age of 4 to 16 years comprising administering orally an effective amount of a tablet comprising the following constituents to said humans:

(a) at least one vitamin, (b) optionally at least one mineral, (c) lysine or a pharmaceutically acceptable salt thereof, (d) at least one sweetener and optionally at least one flavoring agent having the capability of masking the disgusting flavor of lysine, and (e) a pharmaceutically or dietetically acceptable carrier.

This invention also relates to a process for preparing the tablets according to this invention, which consists in the mixing or conjunction of the active ingredients (a), (b) and (c) with the taste masking agent (d) and with one or several carriers (e) such as diluents, excipients, sticking agents, buffering agents, bulk agents, and/or lubricating agents, to realize a pharmaceutical form suitable to be suckled or chewed, such as tablets, or lozenges. This production is obtained according to the known methods of pharmaceutical technology.

The following examples are merely illustrative of the invention without limiting it in any manner.

EXAMPLE I

Tablets to be Sucked

| Component | Function | Declared amount/tablet [mg] |
|---|---|---|
| Active Ingredients (a) + (c) | | |
| (L)-lysine monohydrochloride | essential amino acid | 50.00 |
| Betatab, 10% (E160a) | vitamin | 5.14 (0.514 β-Carotene) |
| Vitamin A palmitate (500000 IU/g) | vitamin | 1.43 (715 IU) |
| Vitamin $B_1$ nitrate (thiamine mononitrate rocoat 33.3%) | vitamin | 1.50 (0.50 Vit. $B_1$ nitrate) |
| Vitamin $B_2$ (Riboflavin rocoat 33.3%) | vitamin | 1.65 (0.55 Vit. $B_2$) |
| Vitamin $B_6$ hydrochloride (Pyridoxine hydrochloride rocoat 33.3%) | vitamin | 1.65 (0.55 Vit. $B_6$ hydrochloride) |
| Vitamin $B_{12}$ (Cyanocobalamin 0.1%) | vitamin | 0.60 (0.60 $10^{-3}$ Vit. $B_{12}$) |
| Vitamin C (Ascorbic acid 90%) | vitamin | 24.44 (22.0 Vit. C) |
| Vitamin $D_3$ (Cholecalciferol 100.000 IU/g) | vitamin | 1.50 (150 IU Vit. $D_3$) |
| Vitamin E acetate (50% d,l-α-tocopherol acetate) | vitamin | 10.43 (5.215 Vit. E acetate) |
| Folic acid | vitamin | 0.05 |
| Biotin | vitamin | 1.50 $10^{-3}$ (15.0 $10^{-3}$ Vit. H) |
| Vitamin PP (Nicotinamide rocoat 33.3%) | vitamin | 18.0 (6.0 Vit. PP) |
| Minerals (b) | | |
| Copper carbonate | mineral | 0.52 |
| Dicalcium phosphate anhydrous | mineral | 220.64 |
| Ferrous (II) fumarate (coated 60%) | mineral | 12.68 |
| Zinc oxide (coated 50%) | mineral | 6.25 |
| Magnesium oxide, heavy | mineral | 19.89 |
| Taste mask (d) | | |
| Aspartame powder | sweetener | 6.00 |

EXAMPLE I-continued

Tablets to be Sucked

| Component | Function | Declared amount/tablet [mg] |
|---|---|---|
| Natural Orange Flavor | flavor | 22.00 |
| Dextrose | sweetener | 275.00 |
| PROSWEET ® | flavor | 4.00 |
| Sorbitol | sweetener/carrier | 597.44 |
| Carrier (e) | | |
| Citric acid | acidifier | 50.00 |
| Silicon dioxide, colloidal | binder | 14.00 |
| Magnesium stearate | lubricant | 12.00 |
| Hydrogenated vegetable oil | diluent | 25.00 |

Once the mixture of components (a), (b), (c) and (d) are perfectly homogenized, the carriers (e) are added thereto. The resulting powder is screened then tableted by direct compression into tablets having a diameter of 16.0 mm, a thickness of 6.5 mm to 7.5 mm, a mean weight of about 1400 mg and a hardness of not more than 200 N.

These tablets show a good geometric stability. They swell into an expanded form, practically equal to that of the starting tablet. They progressively and completely release the active ingredients when in contact with saliva in the mouth.

EXAMPLE II

Determination of the Acceptability of the Tablets According to this Invention The acceptability is determined on a group of 144 healthy children (age 6 to 14 years) which received a tablet which corresponds to the recipe of example 1 containing 50 mg (L)-lysine hydrochloride. Each child chewed this tablet until it has been completely consumed. The children are subsequently interviewed about the taste of the product. The same test is then repeated using different multi-vitamin preparations (Prep A and Prep B) presently on the market which do not contain lysine at all. The following results were obtained:

| | Example 1 (%) | Prep A (%) | Prep B (%) |
|---|---|---|---|
| Observation of behavior: | | | |
| calmly chews the tablet, it seems to taste well | 52 | 63 | 36 |
| Likeability of the taste: | | | |
| very good taste | 33 | 45 | 18 |
| good taste | 28 | 23 | 26 |
| Sweetness of tablets: | | | |
| sweet enough, just right | 70 | 76 | 68 |
| Sourness of tablets: | | | |
| too sour | 29 | 18 | 39 |
| not too sour | 71 | 82 | 61 |
| Feeling in the mouth after chewing: | | | |
| good | 76 | 80 | 58 |
| not so good | 24 | 20 | 42 |
| Interest in eating again: | | | |
| very interested | 20 | 32 | 11 |
| quite interested | 49 | 35 | 35 |

These results clearly show that the tablets according to the present invention despite the high content of (L)-lysine are in the same range of acceptability as Prep A, but are much more acceptable than Prep B.

We claim:
1. A non-effervescing tablet consisting essentially of:
   (a) at least one vitamin;
   (b) at least one mineral selected from the group consisting of: manganese (II) gluconate, copper (II) carbonate, zinc oxide, and magnesium oxide,
   (c) 10-100 mg of lysine or a pharmaceutically acceptable salt thereof;
   (d) at least one sweetener;
   (e) a pharmaceutically or dietetically acceptable carrier; and
   (f) optionally a flavoring agent capable of masking the flavor of lysine,
   wherein said tablet is obtainable by mixing of the different components (a) to (e) and wherein said tablet is formed by direct compression.
2. The tablet according to claim 1, wherein the vitamin is selected from the group consisting of: β-carotene, vitamin A palmitate, vitamin $B_1$ nitrate, vitamin $B_2$, vitamin $B_6$ hydrochloride, vitamin $B_{12}$, vitamin C, vitamin $D_3$, vitamin E acetate, folic acid, vitamin H, and vitamin PP.
3. The tablet according to claim 1, wherein the lysine or a pharmaceutically acceptable salt thereof is (L)-lysine monohydrochloride.
4. The tablet according to claim 1, wherein lysine or a pharmaceutically acceptable salt thereof consists essentially of 10 mg to 100 mg of (L)-lysine monohydrochloride.
5. The tablet according to claim 1, wherein the sweetener is selected from the group consisting of: calcium saccharinate, ammonium cyclamate, ammonium glycirhizinate, aspartame, glucose, and glucitols.
6. The tablet according to claim 1, wherein the flavoring agent is selected from the group consisting of: natural citrus and orange flavor.
7. The tablet according to claim 1, wherein a pharmaceutically or dietetically acceptable carrier is selected from the group consisting of: diluents, excipients, sticking agents, buffering agents, bulk agents, lubricating agents, and colorants.
8. A method of improving the physiological state of a human comprising administering orally to the human an effective amount of a tablet which can be chewed or dissolved in the mouth consisting essentially of:
   (a) a vitamin;
   (b) 10-100 mg of lysine or a pharmaceutically acceptable salt thereof;

(c) a sweetener;
(d) a pharmaceutically or dietetically acceptable carrier;
(e) at least one mineral selected from the group consisting of: manganese (II) gluconate, copper (II) carbonate, zinc oxide, and magnesium oxide; and
(f) optionally a flavoring agent capable of masking the flavor of lysine.

9. A method of improving the development and growth of a child or juvenile comprising administering orally to the child or juvenile an effective amount of a tablet which can be chewed or dissolved in the mouth consisting essentially of:

(a) a vitamin;
(b) 10-100 mg of lysine or a pharmaceutically acceptable salt thereof;
(c) a sweetener;
(d) a pharmaceutically or dietetically acceptable carrier;
(e) at least one mineral selected from the group consisting of: manganese (II) gluconate, copper (II) carbonate, zinc oxide, and magnesium oxide; and
(f) optionally a flavoring agent capable of masking the flavor of lysine.

* * * * *